United States Patent
Tippey et al.

(10) Patent No.: US 8,299,317 B2
(45) Date of Patent: Oct. 30, 2012

(54) ABSORBENT ARTICLES WITH EXTERNAL ACCESS TO INTERNAL CONDUCTORS

(75) Inventors: Darold Dean Tippey, Neenah, WI (US); Andrew Mark Long, Appleton, WI (US); Thomas Michael Ales, III, Neenah, WI (US); Thomas David Ehlert, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 816 days.

(21) Appl. No.: 11/729,702

(22) Filed: Mar. 29, 2007

(65) Prior Publication Data
US 2008/0243099 A1    Oct. 2, 2008

(51) Int. Cl.
*A61F 13/15* (2006.01)
*A61F 13/20* (2006.01)
*A61F 5/48* (2006.01)
*H01H 29/00* (2006.01)
*G08B 23/00* (2006.01)
*G08B 21/00* (2006.01)

(52) U.S. Cl. ........ 604/367; 604/358; 604/361; 604/370; 604/385.01; 128/885; 128/886; 200/61.04; 200/61.05; 340/573.1; 340/573.5; 340/604

(58) Field of Classification Search .................. 604/358, 604/361, 370, 385.01, 367; 128/885, 886; 200/61.05; 340/573.1, 573.5, 604
See application file for complete search history.

(56) References Cited

U.S. PATENT DOCUMENTS

| 3,460,123 | A | * | 8/1969 | Bass | 340/573.5 |
|---|---|---|---|---|---|
| 4,356,818 | A | * | 11/1982 | Macias et al. | 128/886 |
| 4,653,491 | A | * | 3/1987 | Okada et al. | 128/886 |
| 4,732,631 | A | * | 3/1988 | Shimizu | 156/73.3 |
| 4,738,260 | A | * | 4/1988 | Brown | 128/886 |
| 4,768,023 | A | * | 8/1988 | Xie | 340/573.5 |
| 5,009,652 | A | * | 4/1991 | Morgan et al. | 604/385.01 |
| 5,047,283 | A |  | 9/1991 | Leatherman et al. |  |
| 5,264,830 | A |  | 11/1993 | Kline et al. |  |
| 5,469,145 | A | * | 11/1995 | Johnson | 340/604 |
| 5,760,694 | A | * | 6/1998 | Nissim et al. | 340/604 |
| 5,788,797 | A | * | 8/1998 | Herrin et al. | 156/73.1 |
| 5,808,554 | A | * | 9/1998 | Shuminov | 340/604 |
| 5,838,240 | A | * | 11/1998 | Johnson | 340/604 |
| 5,989,370 | A | * | 11/1999 | Wannebo | 156/73.1 |
| 6,200,250 | B1 | * | 3/2001 | Janszen | 493/383 |
| 6,250,929 | B1 |  | 6/2001 | Kolb et al. |  |
| 6,559,772 | B2 | * | 5/2003 | Zand et al. | 340/604 |
| 6,583,722 | B2 |  | 6/2003 | Jeutter et al. |  |
| 6,603,403 | B2 |  | 8/2003 | Jeutter et al. |  |

(Continued)

FOREIGN PATENT DOCUMENTS
EP    1 622 435 A1    2/2006

*Primary Examiner* — Tatyana Zalukaeva
*Assistant Examiner* — Adam Marcetich
(74) *Attorney, Agent, or Firm* — David J. Arteman; Bryan R. Rosiejka

(57) ABSTRACT

An absorbent article includes a liner and an outercover in facing relation and at least one conductive element located between the liner and the outercover. At least a portion of the conductive element is exposed through the liner and/or the outercover to define at least one external contact point. The external contact point defines a perimeter and the liner and/or the outercover is sealed about the perimeter. The contact points provide external access to the internal conductive elements.

20 Claims, 9 Drawing Sheets

U.S. PATENT DOCUMENTS

| | | |
|---|---|---|
| 6,837,976 B2 | 1/2005 | Cai et al. |
| 6,844,504 B2 | 1/2005 | Wang et al. |
| 7,449,614 B2 | 11/2008 | Ales, III |
| 7,489,252 B2 | 2/2009 | Long et al. |
| 7,504,550 B2 | 3/2009 | Tippey et al. |
| 2004/0127867 A1 | 7/2004 | Odorzynski et al. |
| 2004/0147888 A1* | 7/2004 | Huang et al. .......... 604/361 |
| 2005/0156744 A1 | 7/2005 | Pires |
| 2005/0239029 A1 | 10/2005 | Yzermans et al. |
| 2006/0244614 A1 | 11/2006 | Long |
| 2007/0024457 A1 | 2/2007 | Long et al. |
| 2007/0049881 A1 | 3/2007 | Ales et al. |
| 2007/0049882 A1 | 3/2007 | Long et al. |
| 2007/0049883 A1 | 3/2007 | Ales et al. |
| 2007/0049884 A1 | 3/2007 | Long et al. |
| 2007/0083174 A1 | 4/2007 | Ales et al. |
| 2007/0142796 A1 | 6/2007 | Mosbacher et al. |
| 2007/0142797 A1 | 6/2007 | Long et al. |
| 2007/0142799 A1 | 6/2007 | Ales et al. |
| 2007/0252711 A1 | 11/2007 | Long et al. |
| 2007/0252712 A1 | 11/2007 | Allen et al. |
| 2007/0255241 A1 | 11/2007 | Weber et al. |
| 2007/0255242 A1 | 11/2007 | Ales et al. |
| 2007/0282286 A1 | 12/2007 | Collins et al. |
| 2008/0045913 A1 | 2/2008 | Johnson et al. |
| 2008/0052030 A1 | 2/2008 | Olson et al. |
| 2008/0054408 A1 | 3/2008 | Tippey et al. |
| 2008/0057693 A1 | 3/2008 | Tippey et al. |
| 2008/0058740 A1 | 3/2008 | Sullivan et al. |
| 2008/0058741 A1 | 3/2008 | Long et al. |
| 2008/0058743 A1 | 3/2008 | Cohen et al. |
| 2008/0058745 A1 | 3/2008 | Long et al. |
| 2008/0082062 A1 | 4/2008 | Cohen et al. |
| 2008/0082063 A1 | 4/2008 | Ales et al. |
| 2008/0132858 A1 | 6/2008 | Tippey et al. |

\* cited by examiner

ABSORBENT ARTICLES WITH EXTERNAL ACCESS TO INTERNAL CONDUCTORS

BACKGROUND OF THE INVENTION

Absorbent articles such as diapers, training pants, incontinence products, feminine hygiene products, swim undergarments, and the like conventionally include a liquid permeable body-side liner, a liquid impermeable outercover, and an absorbent core located between the outercover and the liner for taking in and retaining liquids (e.g., urine) exuded by the wearer.

Some absorbent articles further include various sensing circuits and signaling devices that produce a visual and/or an audible alarm when certain conditions are detected. Generally, the sensing circuits have been located within the absorbent articles and the signaling devices have been externally located on the absorbent article.

For proper operation, the signaling devices need to be electrically connected with the sensing circuits but typically one or more non-conductive layers are interposed therebetween. As such, various solutions have been proposed for reliably creating an electrical connection between the internal sensing circuit and the external signaling device. For example, it has been suggested that the non-conductive layer be slit, cut, or apertured to create openings to provide access to the sensing circuit lying below the non-conductive layer. However, these systems may be less desirable because precise registration control may be required to ensure that the openings are aligned with the conductive elements. This may complicate converting processes and increase cost and delay. Furthermore, these systems may be less desirable because the openings in the outercover and/or liner may increase the possibility of body fluid escaping from the absorbent article.

Other methods of creating an electrical connection have included signaling devices with conductive contacts adapted to pierce the non-conductive layers to contact the conductive sensing circuit located inside the absorbent articles. However, these systems may not result in reliable connections because the intervening layers of nonconductive materials may inhibit continuity between the signaling device and the conductive sensing circuit. Additionally, these systems also may increase the possibility of body fluid escaping from the absorbent article particularly if several penetration attempts are made before a proper connection is formed. Finally, these systems may require the signaling device to be in contact with the body of the wearer which may be less comfortable than a signaling device located only on a garment side of the absorbent article.

Therefore, there remains a need for an absorbent article that is adapted to provide a reliable connection between an internally positioned sensing circuit and an externally mounted signaling device while minimizing the shortcomings of the prior art.

SUMMARY OF THE INVENTION

In one aspect, the present invention provides an absorbent article having a liner and an outercover in facing relation with at least one conductive element located between the liner and the outercover. At least a portion of the conductive element is exposed through at least one of the liner and the outercover to define at least one external contact point. The at least one external contact point defines a perimeter and at least one of the liner and the outercover is sealed about the perimeter. In some embodiments, the absorbent article may include at least one external contact point that extends at least partially through the outercover. In some embodiments, the conductive elements are intact proximate the external contact points. In some embodiments, the conductive element is a laminate that includes a conductive layer and a masking layer. The conductive element may be oriented towards the outercover and the masking layer may be oriented towards the liner.

In some embodiments, the absorbent article may have a length and first and second conductive elements extending the length of the absorbent article. In some embodiments, the first conductive element and the second conductive element may have a plurality of portions extending at least partially through the outercover to define a plurality of external contact points. In some embodiments, the outercover and the liner may be joined together at bond points that do not include the conductive element.

In another aspect, the present invention provides a kit. The kit may include any of the absorbent articles described herein and a signaling device. In some embodiments, the absorbent article may include a plurality of external contact points formed in the shape of a first indicia and the signaling device may include a second indicia wherein the first and second indicia facilitate the alignment of the signaling device, relative to the absorbent article.

In some embodiments, an absorbent article may have a length and include a liner and an outercover in facing relation. The absorbent article may also include a first conductive element and a second conductive element located between the liner and the outercover and extending the length of the absorbent article. The absorbent article may also include a plurality of portions of the first conductive element and the second conductive element that are at least partially exposed through the outercover to define a plurality of external contact points. Each external contact point defines a perimeter and the outercover may be sealed about each perimeter.

In some embodiments, the liner and the outercover may be joined together at bond points in areas that do not include the first or the second conductive elements. In some embodiments, the absorbent articles may include a plurality of external contact points wherein the plurality of external contact points are adapted to provide a first indicia for aligning a signaling device with the absorbent article to ensure electrical connectivity. In some embodiments, the absorbent article may be provided in a kit with a signaling device having a second indicia that is adapted to align with the first indicia to ensure proper electrical connectivity.

In another aspect, the present invention provides a method of exposing portions of internally positioned conductive elements to an external surface of an absorbent article. The method includes providing an outercover and liner in facing relation with a conductive element located therebetween; at least partially exposing a portion of the conductive element through the outercover to define at least one external contact point on an outer article surface; and sealing the outercover about a perimeter of the at least one external contact point by at least partially melting portions of the outercover.

In some embodiments, the method includes providing the outercover, the liner, and the conductive element as a part of an interconnected web of absorbent articles. In some embodiments, the method includes exposing a portion of the conductive element by using pressure bonding, ultrasonic bonding, or thermal bonding. In some embodiments, the method includes exposing a portion of the conductive element at least partially through the outercover.

In some embodiments, the steps of exposing a portion of the conductive element and sealing the outercover may occur in the same operation. In some embodiments, the conductive element may be a laminate having a conductive layer and a masking layer and the method may include orienting the conductive layer towards the outercover and orienting the masking layer towards the liner. In some embodiments, the method may include bonding the outercover and the liner at bond points that do not include the conductive element in the same operation as the exposing step.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

DETAILED DESCRIPTION OF THE INVENTION

Figure 1:
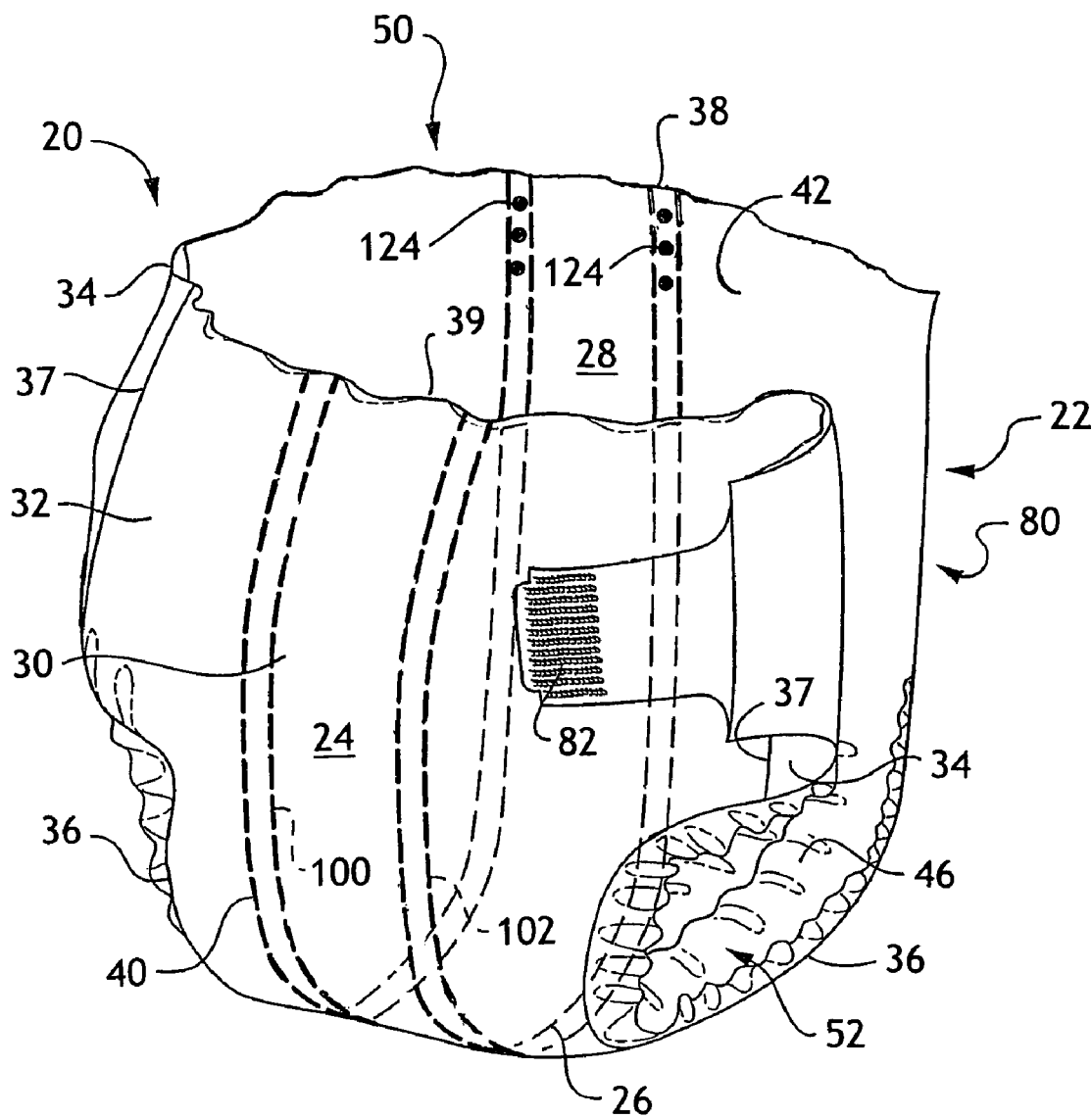
FIG. 1 is a rear perspective view of one embodiment of an absorbent article made in accordance with the present invention.

It is to be understood by one of ordinary skill in the art that the present discussion is a description of exemplary embodiments only, and is not intended as limiting the broader aspects of the present invention.

In one aspect, the present invention provides absorbent articles adapted to be joined with a signaling device that may be configured to indicate the presence of a body fluid in the absorbent article or other changes in the condition of the product or wearer. The absorbent article may be, for instance, a diaper, a training pant, an incontinence product, a feminine hygiene product, a medical garment, a bandage, or the like. Absorbent articles made according to the present disclosure may include an open circuit that becomes closed when a conductive fluid, such as a body fluid, is sensed in between a pair of conductive elements. Generally, the absorbent articles containing the open circuit are disposable meaning that they are designed to be discarded after a limited use rather than being laundered or otherwise restored for reuse.

The open circuit contained within the absorbent articles of the present disclosure is configured to be joined with a signaling device. The signaling device can provide power to the open circuit while also including some type of audible and/or visible signal that indicates to the user the presence of a body fluid. Although the absorbent article itself is disposable, the signaling device may be reusable from article to article. In this regard, the present disclosure is particularly directed to absorbent articles adapted to provide convenient and reliable connection between the open circuit positioned inside the absorbent article and the signaling device located outside the absorbent article.

As described above, the open circuit in combination with the signaling device may be configured to indicate the presence of a body fluid contained within the absorbent article. The particular targeted body fluid may vary depending upon the particular type of absorbent article and the desired application. For instance, in one embodiment, the absorbent article comprises a diaper, a training pant, or the like and the signaling device is configured to indicate the presence of urine and/or any component of urine. Additionally, the signaling device may be configured to indicate the presence of a metabolite that may indicate the presence of a diaper rash. For adult incontinence products and feminine hygiene products, on the other hand, the signaling device may be configured to indicate the presence of a yeast or of a particular constituent in urine, such as a polysaccharide.

Referring to FIGS. 1-4, for exemplary purposes, an absorbent article 20 that may be made in accordance with the present invention is shown. The absorbent article 20 may or may not be disposable. It is understood that the present invention is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

Figure 3:
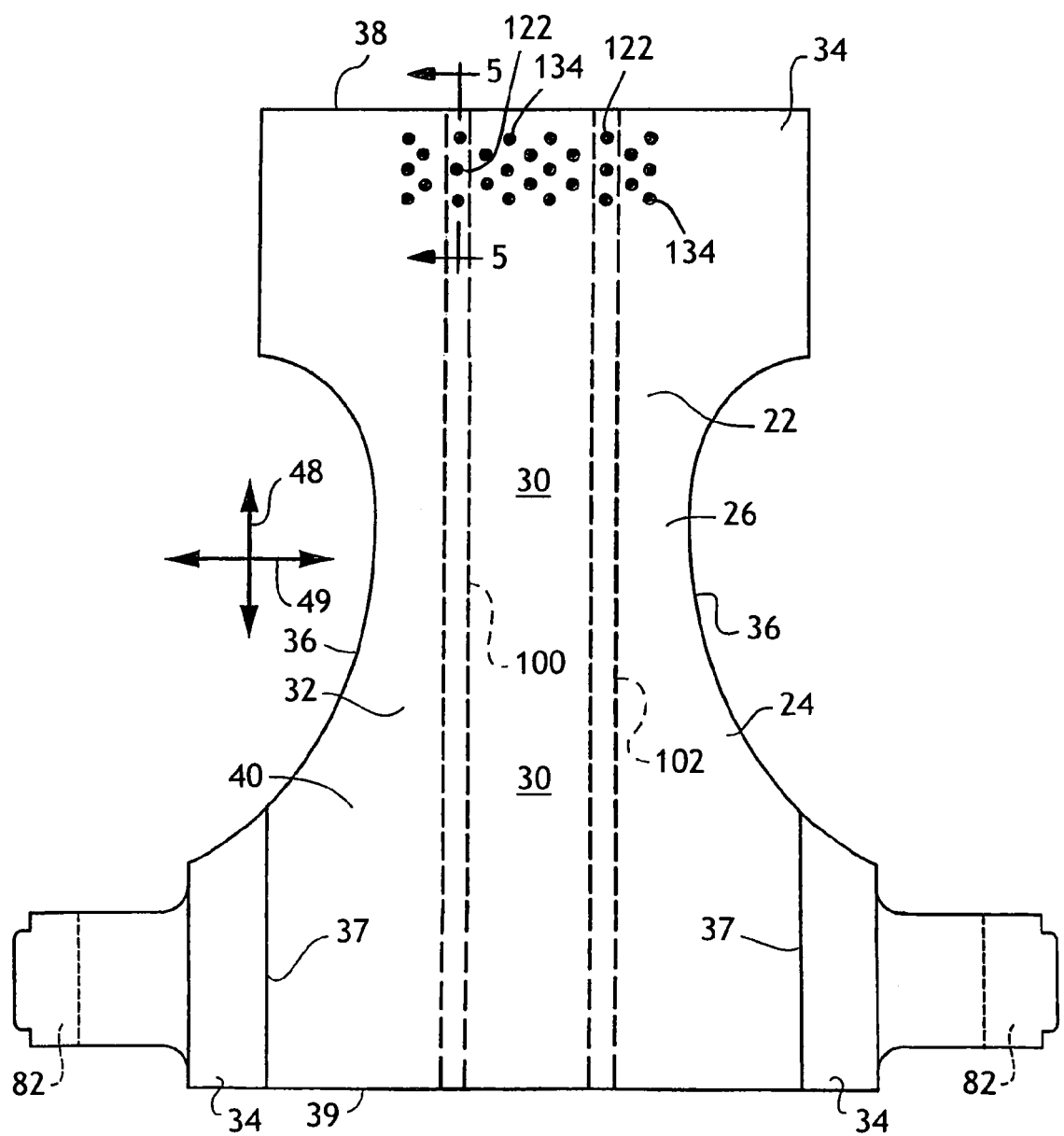
FIG. 3 is a plan view of another embodiment of an absorbent article made in accordance with the present invention wherein the article is illustrated in an unfastened, unfolded and laid flat condition showing the surface of the article that faces away from the wearer.
Figure 4:
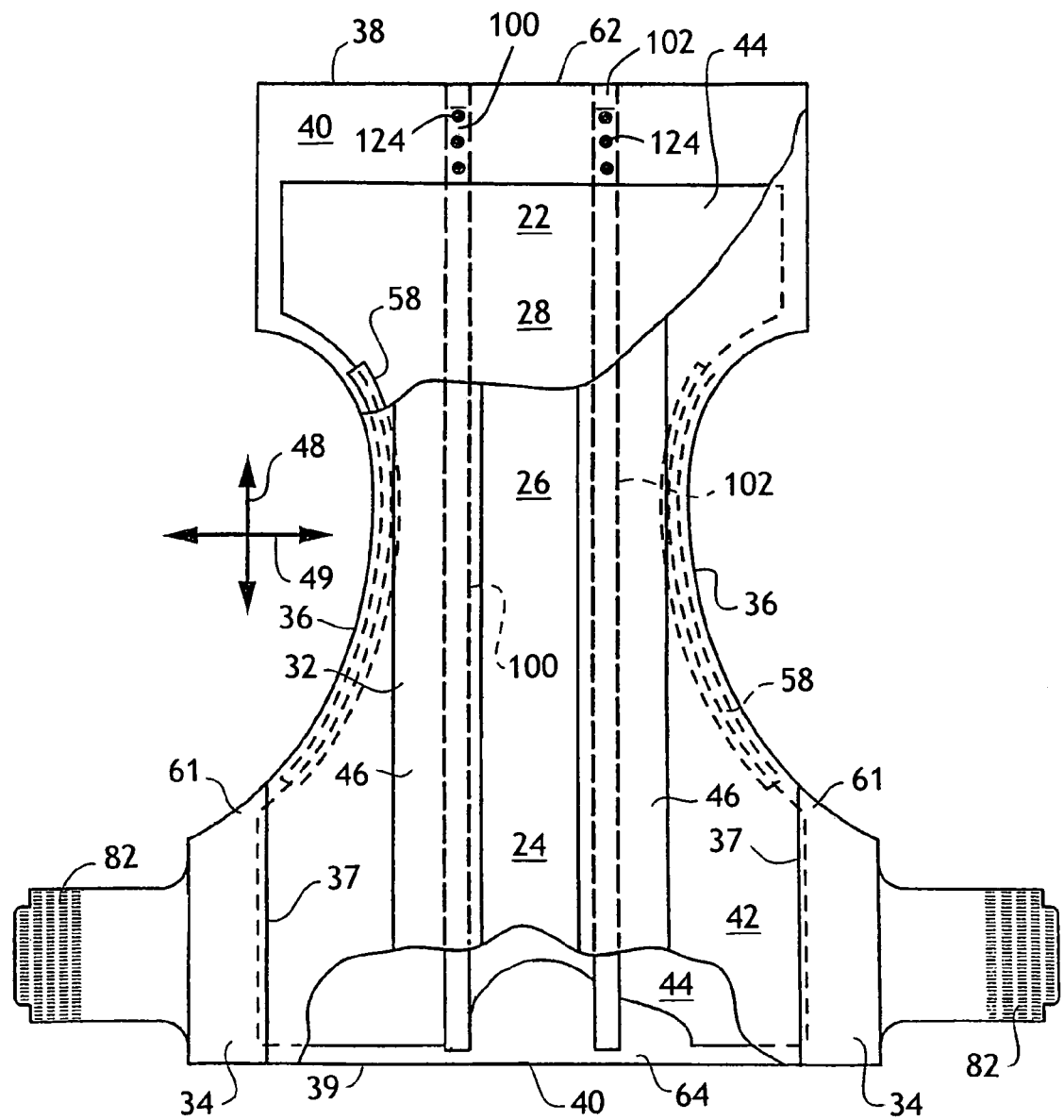
FIG. 4 is a plan view of the absorbent article of FIG. 1 showing the surface of the absorbent article that faces the wearer when worn and with portions cut away to show underlying features.

A diaper 20 is representatively illustrated in FIG. 1 in a partially fastened condition. A diaper 20 is also represented in FIGS. 3 and 4 in an opened and unfolded state. FIG. 3 is a plan view illustrating the exterior side of a diaper 20, while FIG. 4 illustrates the interior side of a diaper 20. As shown in FIGS. 3 and 4, the diaper 20 defines a longitudinal direction 48 that extends from the front of the article when worn to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner article surface 28 adapted in use, i.e., positioned relative to the other components of the article 20, to be disposed toward the wearer, and an outer article surface 30 opposite the inner surface. The front and back regions 22 and 24 are those portions of the diaper 20, which when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in various embodiments, encompasses the front region 22, the back region 24, and the crotch region 26. Referring to FIGS. 1-4, the chassis 32 includes an outercover 40 and a bodyside liner 42 that may be joined to the outercover 40 in a superimposed relation therewith by adhesives, ultrasonic bonds, thermal bonds or other conventional techniques. Referring to FIG. 4, the liner 42 may suitably be joined to the outercover 40 along the perimeter of the chassis 32 to form a front waist seam 62 and a back waist seam 64. As shown in FIG. 4, the liner 42 may suitably be joined to the outercover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outercover 40 and the bodyside liner 42 for absorbing liquid body exudates exuded by the wearer, and may further include a pair of containment flaps 46 secured to the bodyside liner 42 for inhibiting the lateral flow of body exudates.

The outercover layer 40 may be constructed of any operative material, and may or may not be configured to be operatively liquid-permeable. In a particular configuration, the outercover layer 40 may be configured to provide an operatively liquid-impermeable layer. The outercover layer may, for example, include a polymeric film, a woven fabric, a nonwoven fabric or the like, as well as combinations or composites thereof. For example, the outercover layer 40 may include a polymer film laminated to a woven or nonwoven fabric. In a particular feature, the polymer film can be composed of polyethylene, polypropylene, polyester or the like, as well as combinations thereof. Additionally, the polymer film may be micro-embossed. Desirably, the outercover layer 40 can operatively permit a sufficient passage of air and moisture vapor out of the article while blocking the passage of bodily liquids.

The liner 42 may be constructed of any operative material, and may be a composite material. For example, the liner 42 can include a woven fabric, a nonwoven fabric, a polymer film, or the like, as well as combinations thereof. Examples of a nonwoven fabric include, spunbond fabric, meltblown fabric, coform fabric, a carded web, a bonded-carded-web, or the like as well as combinations thereof. For example, the liner 42 can include a woven fabric, a nonwoven fabric, a polymeric film that has been configured to be operatively liquid-permeable, or the like, as well as combinations thereof. Other examples of suitable materials for constructing the liner 42 can include rayon, bonded-carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis.

To further enhance containment and/or absorption of body exudates, the diaper 20 may also suitably include leg elastic members 58 (FIG. 4), as are known to those skilled in the art. The leg elastic members 58 can be operatively joined to the outercover 40 and/or the bodyside liner 42 and positioned in the crotch region 26 of the absorbent article 20.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive.

As shown in FIGS. 1-4, absorbent articles 20 may further include a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis 32 along a pair of opposing longitudinal edges 37. The side panels 34 may be attached or bonded to the chassis 32 using any suitable bonding technique. For instance, the side panels 34 may be joined to the chassis 32 by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, the outercover 40, or both the bodyside liner 42 and the outercover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIG. 1, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant, absorbent swimwear, and the like.

The fastening system 80 may include laterally opposite first fastening components 82 adapted for refastenable engagement to corresponding second fastening components 84. In the embodiment shown in FIG. 2, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, and the like, and combinations thereof.

In the embodiments illustrated in FIGS. 1, 3, and 4, the first fastening components 82 include hook fasteners and the outercover 40 serves as the second fastening component 84. In the illustrated aspect of FIG. 2, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like.

Figure 2:
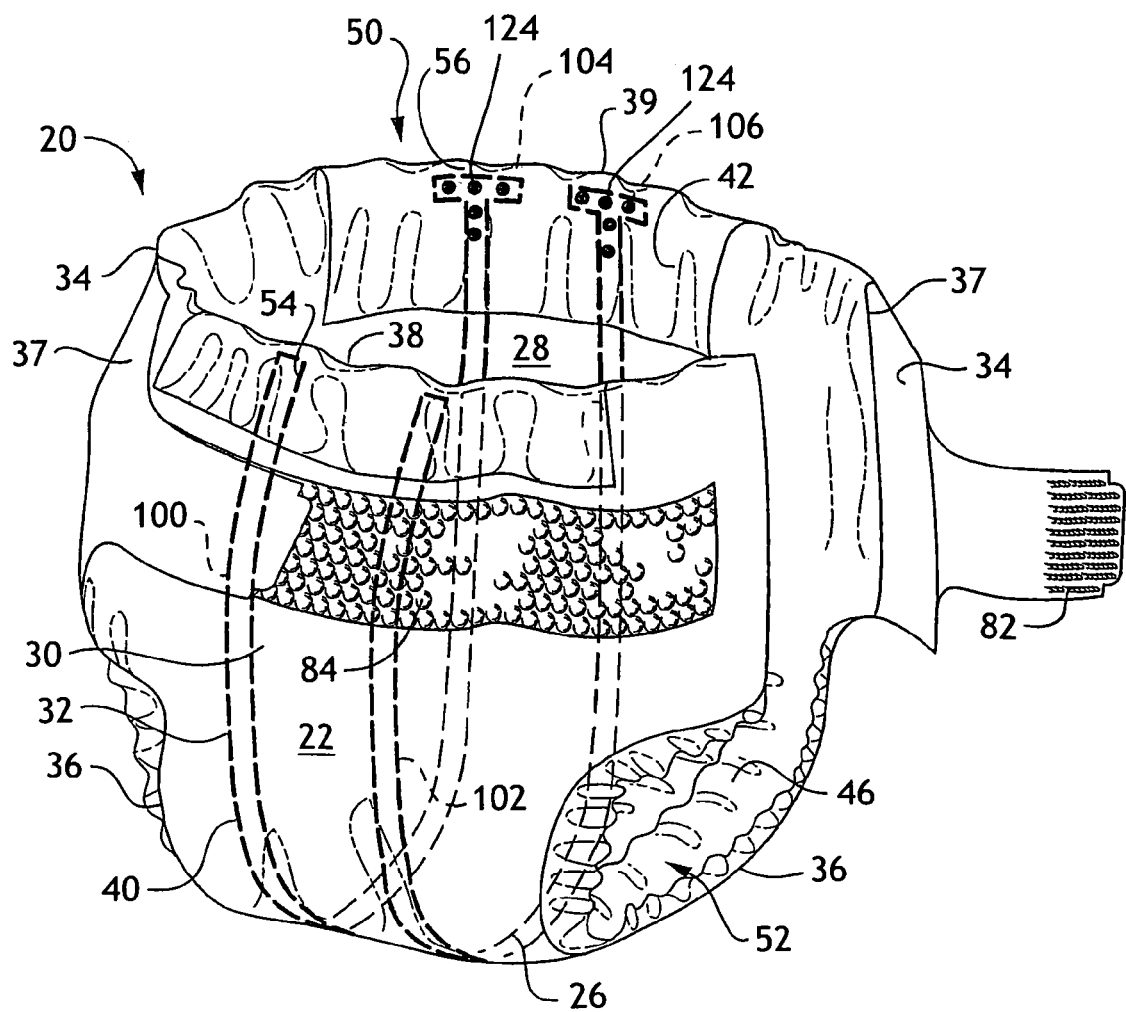
FIG. 2 is a front perspective view of another embodiment of an absorbent article made in accordance with the present invention.

In addition to possibly having elastic side panels, the absorbent article 20 may include various waist elastic members for providing elasticity around the waist opening. For example, as shown in FIG. 2, the absorbent article 20 can include a front waist elastic member 54 and/or a back waist elastic member 56.

As described above, the present disclosure is particularly directed to incorporating a body fluid indicating system, such as a wetness indicating system into the absorbent article 20. In this regard, as shown in FIGS. 1-4, the absorbent article 20 may include a first conductive element 100 spaced from a second conductive element 102. In these embodiments, the conductive elements extend from the front region 22 of the absorbent article to the back region 24 without intersecting. The conductive elements 100 and 102 can comprise any suitable conductive material, such as a conductive thread or a conductive foil. The first conductive element 100 does not intersect the second conductive element 102 in order to form an open circuit that may be closed, for instance, when a conductive fluid is positioned in between the conductive elements. In other embodiments, however, the first conductive element 100 and the second conductive element 102 may be connected to a sensor within the chassis. The sensor may, for example, be used to sense changes in temperature and/or may be used to sense the presence of a particular substance in urine or other body exudates.

In the embodiment shown in FIG. 1, the conductive elements 100 and 102 extend the entire length of the absorbent article 20. It should be understood, however, that in other embodiments the conductive elements may extend only to the crotch region 26 or may extend to any particular place in the absorbent article where a body fluid is intended to be sensed.

The conductive elements 100 and 102 may be incorporated into the chassis 32 at any suitable location as long as the conductive elements are positioned so as to contact a body fluid that is absorbed by the absorbent article 20. In this regard, the conductive elements 100 and 102 generally lie inside the outercover 40. In one embodiment, the conductive elements 100 and 102 may be attached or laminated to the inside surface of the outercover 40 that faces the absorbent structure 44. Alternatively, the conductive elements 100 and 102 may be positioned on the absorbent structure 44 or positioned on the liner 42.

In order for the internally positioned conductive elements 100 and 102 to be easily connected to an externally mounted signaling device, the present invention provides an absorbent article having portions of the conductors 100 and/or 102 at least partially exposed through one or more non-conductive layers to define one or more external contact areas 120 having one or more external contact points 122. See for example, FIG. 5 which is a cross sectional view of the absorbent article of FIG. 3 taken along the line 5-5.

Figure 5:
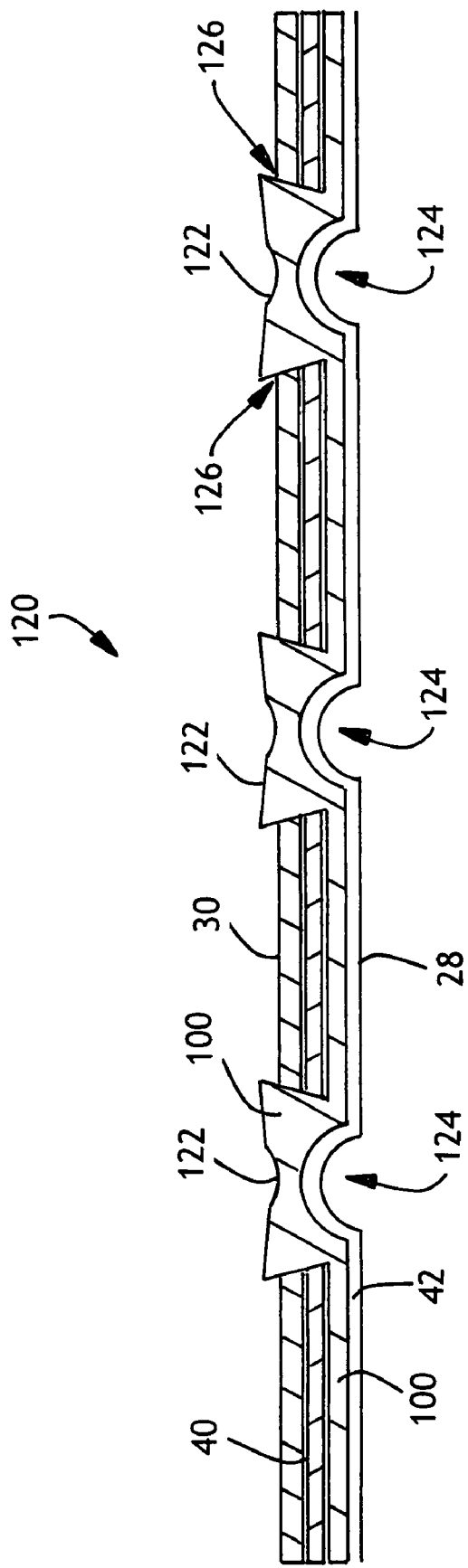
FIG. 5 is a magnified cross-sectional view of the absorbent article of FIG. 3 taken along the line 5-5.

Referring now to FIG. 5, the absorbent article 20, in the portions illustrated, includes a laminate comprising an outercover 40, a first conductive element 100, and a liner 42. In various embodiments, and as illustrated in FIG. 5, the outercover 40 may include a laminate of two or more materials as is known in the art. For example, the outercover 40 may be a laminate including a liquid impervious film layer and a nonwoven "cloth-like" layer as is known in the art. The outercover 40 defines the outer article surface 30 whereas the liner 42 defines the inner article surface 28. Portions of the first conductive element 100 are at least partially exposed through the outercover 40 to the outer surface 30 to define one or more external contact points 122. The contact points 122 collectively define an external contact zone 120 adapted for electrical connection with a signaling device.

The contact points 122 may have any suitable size, shape, and surface area. For example, the contact points 122 may be generally circular and have a diameter of 0.1 to 5 mm, 0.5 to 2 mm, or about 1 mm. In some embodiments, the individual contact points 122 may have a surface area of at least 0.1 mm$^2$, at least 1.0 mm$^2$, or at least 2.0 mm$^2$. In some embodiments, the individual contact points 122 may have a surface area of about 3 mm$^2$. Any number of contact points 122 may be included and the individual contact points 122 may have different shapes and may be provided in any suitable combination of shape, size, and/or pattern to form an external contact zone 120. Likewise, the external contact zone 120 may have any suitable size, shape, and surface area. In some embodiments, the external contact area 120 may be expressed as the percentage of the exposed conductor surface area as compared to the total area. In some embodiments, the external contact area 120 may include 5 to 50 percent or 20 to 40 percent conductive surface area.

In some embodiments, the contact points 122 may include indentations 124 on the inner surface 28 corresponding to the contact points 122. For example, as illustrated in FIGS. 1, 2, and 5 indentations 124 are present on the inner surface 28 and correspond with external contact points 122 exposed on the outer surface 30 (visible in FIGS. 3 and 5).

The external contact points 122 define a contact point perimeter 126. In some embodiments, the material, through which the external contact points 122 are exposed, may be sealed about the contact point perimeter 126 thereby inhibiting the passage of fluid through the material at these locations. See for example FIG. 5 wherein the external contact points 122 are exposed through the outercover 40 and wherein the outercover 40 is sealed about the contact point perimeter 126 to prevent fluid escape therethrough.

In some embodiments, the outercover 40 may be sealed about the perimeter 126 of external contact points 122 such that portions of the outercover with external contact points 122 have at least as much resistance to fluid passage as those portions of the outercover 40 having no external contact points 122 exposed therethrough. In other words, in some embodiments, there is no detriment to the liquid impermeability of the outercover 40 due to the external contact points 122.

In some embodiments, portions of the first conductive element 100 and/or the second conductive element 102 may be exposed and/or extend at least partially through the liner 42 to the inner article surface 28 to define one or more external contact points 122 (not shown). The contact points 122 collectively define an external contact area 120 adapted for electrical connection with a signaling device. In some embodiments, the contact points 122 may include indentations 124 on the outer surface 30 corresponding to the contact points 122. In some embodiments, portions of the first conductive element 100 and/or portions of the second conductive element 102 may be at least partially exposed and/or extended through both the liner 42 and the outercover 40 to define external contact points 122 on the inner article surface 28 and/or the outer article surface 30. In such embodiments, the signaling device may suitably be connected with either or both surfaces.

In various embodiments, portions of the first conductive element 100 and/or the second conductive element 102 may extend at least partially through the liner 42 and/or the outercover 40. In some embodiments, portions of the first conductive element 100 and/or the second conductive element 102 may extend at least partially through the liner 42 and/or the outercover 40 without rupturing the conductive elements 100 and/or 102. For example, in FIG. 5, portions of conductive element 100 extend completely through the outercover 40 and are intact, i.e., not ruptured, torn, or otherwise discontinuous. In some embodiments, all portions of the first element 100 and all portions of the second conductive element 102 are intact. Maintaining the conductive elements intact is believed to be advantageous because more continuity results in better reliability of the body fluid indicating system.

In some embodiments, the absorbent article may include a plurality of bond points 134 and a plurality of external contact points 122. For example, as illustrated in FIG. 3, an absorbent article 20 may include conductive elements 100 and 102 located between a liner and an outercover. The absorbent article 20 may also include a plurality of bond points 134 between the outercover and liner in locations that do not include the conductive elements 100 and 102. Likewise, the absorbent article 20 may include external contact points 122 in locations that include the conductive elements 100 and 102 between the liner and the outercover.

In order for the conductive elements 100 and 102 to be easily connected to a signaling device, the first conductive element 100 may be attached to and/or include a first conductive pad member 104, while the second conductive element 102 may be connected to and/or include a second conductive pad member 106. Likewise, portions of the first conductive pad member 104 and/or portions of the second conductive pad member 106 may be exposed and/or extended through the outercover 40 and/or the liner 42 to define external contact points 122 as described herein.

The pad members 104 and 106 may be provided for making a reliable connection between the open circuit formed by the conductive elements to a signaling device that is intended to be installed on the chassis by the consumer. In particular, the external contact points 122 associated with the pad members 104 and 106 may create a larger target zone for attaching the signaling device to the conductive elements.

The position of the conductive pad members 104 and 106 on the absorbent article 20 can vary depending upon where it is desired to mount the signaling device. For instance, in FIG. 2, the conductive pad members 104 and 106 are positioned in the back region 24 along the waist opening of the article. It should be appreciated, however, that in other embodiments, the absorbent article 20 may include conductive pad members being positioned at either or both ends of each conductive element 100 and 102. In this manner, a user can determine whether or not to install the signaling device on the front or the back of the article. In still other embodiments, it should be understood that the pad members may be located along the side of the article or towards the crotch region of the article.

Figure 6:
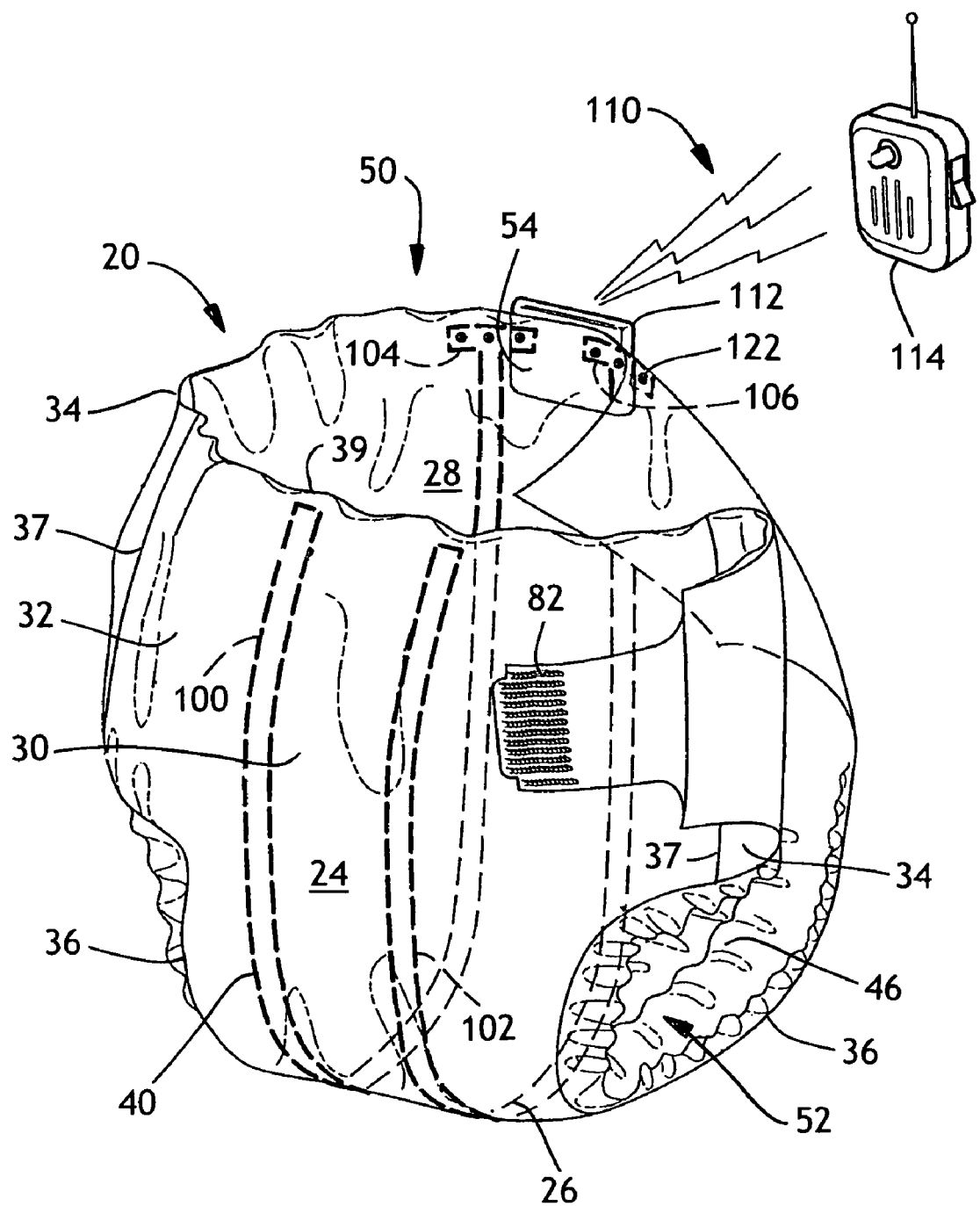
FIG. 6 is a perspective view of the embodiment shown in FIG. 2 further including an exemplary signaling device.

Referring to FIG. 6, for exemplary purposes, a signaling device 110 is shown attached to the external contact points 122. As shown, in this embodiment, a signaling device 110 includes a transmitter 112 and a receiver 114. The transmitter 112 may include two or more terminals that are electrically connected to the first and second conductive elements 100 and 102 via the external contact points 122. When a body fluid is present in the absorbent article 20, the open circuit formed by the conductive elements 100 and 102 is closed which, in turn, activates the signaling device 110. In particular, in this embodiment, the transmitter 112 sends a wireless signal to the receiver 114 which then indicates to a user that a body fluid is present in the absorbent article.

The signaling device 110 can emit an audible signal or a visual signal in order to indicate to the user that the circuit has been closed. The audible signal, for instance, may be as simple as one or more beeps to perhaps emitting a musical tune. Similarly, if the signaling device 110 issues a visible signal, the visible signal may comprise a few lights or an interactive display. In still another embodiment, the receiver 114 of the signaling device 110 may be configured to vibrate when the circuit within the absorbent article is closed.

As described above, the signaling device 110 can be configured to indicate the presence of any suitable conductive fluid within the absorbent article 20. The fluid may comprise, for instance, urine, a metabolite, and the like.

In the embodiment shown in FIG. 6, the signaling device 110 includes a transmitter 112 in combination with a receiver 114. It should also be understood, however, that the signaling device may comprise a single unit that remains attached to the absorbent article 20. For example, the signaling device may be mounted on the absorbent article and issue a visible signal and/or an audible signal from the signaling device itself.

As discuss above, typical body fluid indicating systems require penetration through one or more layers to create contact between the conductive elements and the signaling device. The present invention includes one or more external contact points 122 exposed to the surface of the article (inner surface 28 and/or outer surface 30) to provide direct surface to surface contact with the terminals of the signaling device. Therefore, any suitable means of attaching the signaling device to the absorbent article may be used. For example, in various embodiments, the signaling device may be attached to the absorbent article with adhesives, cohesives, hook and loop systems, snaps, buttons, and the like, and combinations thereof. Additionally or alternatively, the signaling device may be placed in a pocket or otherwise physically retained in proximity to the external contact points 122 to establish electrical conductivity therebetween.

In some embodiments, the external contact points 122 may be arranged such that the external contact area 120 has any suitable shape, size, design, or configuration. For example, referring to FIG. 3, the external contact points 122 are generally arranged in two parallel lines extending in the longitudinal direction 48 and corresponding with the first and the second conductive elements 100 and 102. In some embodiments, the external contact points 122 may be arranged to resemble a target, arrows, letters, dots, shapes, or other indicia that may assist in the proper alignment of a signaling device with the conductive elements.

Figure 7:
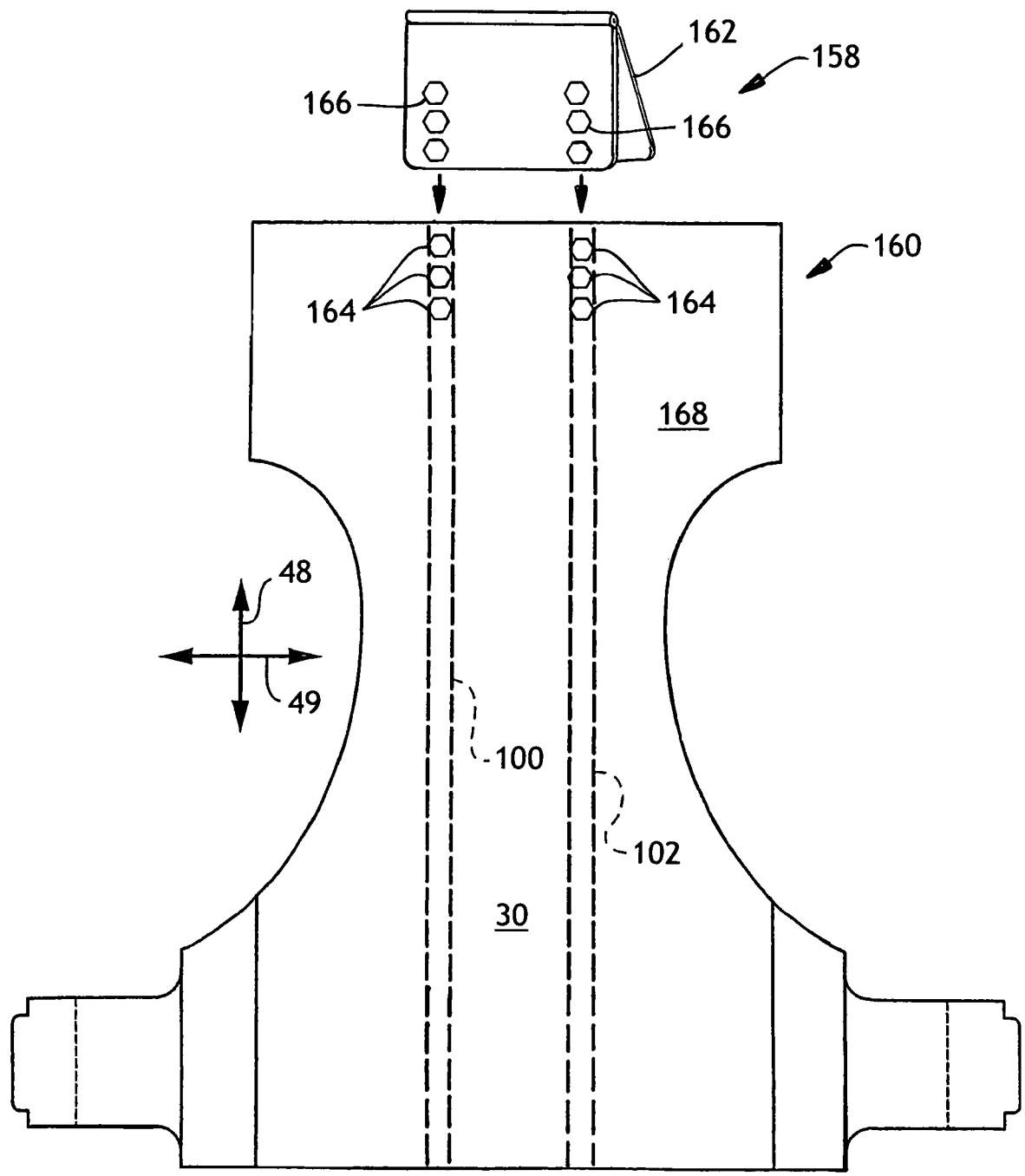
FIG. 7 representatively illustrates an exemplary kit of the present invention.

For example, FIG. 7 representatively illustrates an absorbent article 160 and a signaling device 162. In some embodiments, the absorbent article 160 and the signaling device 162 may be a kit 158. The absorbent article 160 includes a first conductive element 100 and a second conductive element 102. Portions of the conductive elements 100 and 102 are at least partially exposed through the outercover 168 to define a plurality of external contact points 164. In the illustrated embodiment, the external contact points 164 are shaped like hexagons.

In some embodiments, the signaling device 162 may include one or more indicia 166 and the external contact points may be arranged in the same shape, pattern, and/or size as the indicia 166. For example, as illustrated in FIG. 7, the signaling device 162 has an indicia 166 made up of a series of hexagon shapes and the external contact points 164 are sized, shaped, and positioned such that aligning the indicia 166 of the signaling device 162 with the external contact points 164 assures that the electrical terminals of the signaling device 162 are aligned with the external contact points 164 of the conductive elements 100 and 102.

The conductive elements 100 and/or 102 may include any suitable conductive material. In some embodiments, the conductive elements 100 and/or 102 can include conductive thread, conductive foil, and the like, and combinations thereof. In some embodiments, the conductive elements 100 and/or 102 may be a laminate made of two or more layers of material wherein at least one of the layers is conductive. In some embodiments, the conductive elements 100 and/or 102 may include a conductive layer oriented towards the outercover 40 and a second layer oriented towards liner 42. In some embodiments, the second layer may be a masking layer.

Figure 8:
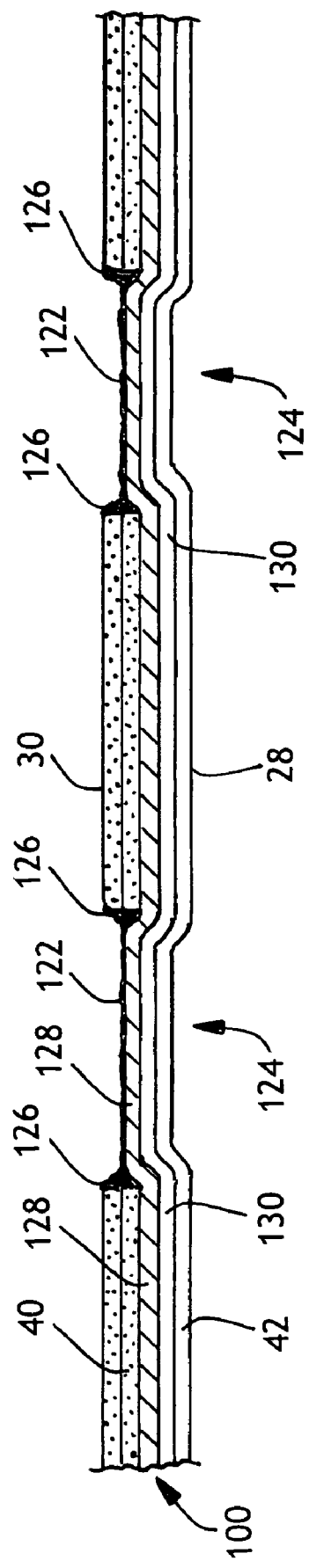
FIG. 8 is an exemplary cross-sectional view of one embodiment of the present invention.

As used herein, the term "masking layer" refers to a layer of material having a color and/or pattern similar to the color and/or pattern of an overlaying material such that the masking layer is less visually noticeable. For example, FIG. 8 representatively illustrates a cross-sectional view similar to FIG. 5. FIG. 8 illustrates a liner 42 defining an inner article surface 28 and an outercover 40 defining an outer article surface 30. Positioned between the liner 42 and the outercover 40 is a conductive element 100. The conductive element 100 includes a conductive layer 128 and a masking layer 130 laminated together. The conductive layer 128 is oriented towards the outercover 40 whereas the masking layer 130 is oriented towards the liner 42. Portions of the conductive element 100 are exposed through the outercover 40 to define external contact points 122. Each external contact point 122 defines a contact point perimeter 126. In various embodiments, the outercover 40 may be sealed about the contact point perimeter 126 to prevent fluid passage there through.

In some embodiments, the liner 42 may be white and the conductive elements 100 and/or 102 may include a masking layer 130 that is also white. In these embodiments, the conductive layer 128 of elements 100 and/or 102 may be less visible through the liner 42 because of the masking layer 130.

The conductive elements 100 and/or 102 may have any suitable thickness and/or width. For example, in some embodiments, the conductive elements 100 and/or 102 may have a thickness of 25-4000 angstroms, 50-2000 angstroms, or 100-500 angstroms. Suitable conductive materials include NEPTAPE 1001 laminated foil available from NEPTCO having offices at 30 Hamlet St., Pawtucket, R.I., USA. NEPTAPE 1001 is a laminate having a 12 micron layer of polyester film and a 12 micron layer of aluminum film. Other suitable conductive materials include vapor deposited films such as those available from Vacumet Corporation having offices at 22 Riverview Drive, Wayne, N.J., USA.

In another aspect, the present invention provides a method of exposing portions of one or more internally positioned conductive materials to an external surface of an absorbent article. The method includes providing at least one conductive material and at least one non-conductive material. The method further includes exposing and/or extending one or more portions of the conductive material at least partially through the non-conductive material to define one or more external contact points. The exposing step may include ultrasonic bonding, pressure bonding, thermal bonding, and the like. The method may further include forming a seal about the contact points such that the non-conduct material remains liquid impermeable. The seal may result from portions of the non-conductive layers melting and flowing around the external contact point perimeter. The method may further include locating the conductive material between the first non-conductive material and a second non-conductive material to form an absorbent article wherein the external contact points are exposed to an inner and/or outer article surface. As used herein, the term "directed" describes the act of moving a first object through or towards a second object or surface.

In some embodiments, the method of exposing an internally positioned conductive material to an external surface of an absorbent article includes providing an outercover and liner in facing relation. The method may further include providing at least one conductive material located between the outercover and liner material. The method may further include at least partially exposing one or more portions of the conductive material through the outercover and/or the liner to define one or more external contact points. The exposing step may include ultrasonic bonding, pressure bonding, thermal bonding, and the like. In some embodiments, the method may further include sealing the outercover and/or the liner about the external contact points. The sealing may result from portions of the liner, outercover, adhesives, or combinations thereof experiencing localized melting thereby permitting material to flow around the external contact points. In some embodiments, the liner and the outercover may be bonded in locations that include the conductive material therebetween and in locations that do not include the conductive material therebetween. In other words, the outercover, conductive material, and liner laminate may include a plurality of bond points, some resulting in external contact points and some absent external contact points. As such, precise registration is not necessary to create the external contact points because a wide path of bonding can be created. When the conductive material is present, portions corresponding to the bond pattern will be exposed, at least partially, through the material. When the conductive material is not present, the outercover and liner will merely be bonded together as illustrated in FIG. 3.

In some embodiments, the method of exposing an internally positioned conductive material to an external surface of an absorbent article includes providing an outercover and at least one conductive material in facing relation therewith. The method may further include directing one or more portions of the conductive material at least partially through the outercover to define one or more external contact points. The directing step may include the use of ultrasonic bonding, thermal bonding, pressure bonding, and the like. The method may further include the step of sealing the outercover about the external contact points to maintain the liquid impermeability of the outercover. The method may further include providing a liner in facing relation with the outercover such that the conductive material is located between the outercover and the liner and the external contact points are exposed to an outer article surface.

In some embodiments, the method may include providing an interconnected web of absorbent articles having at least one conductive material located therein. The interconnected web of absorbent articles may be subjected to a bonding process wherein at least a portion of the conductive material is directed towards and/or exposed to the outer article surface or inner article surface to define external contact points.

In various embodiments, the bonding process may cause one or more materials to flow proximate the location of the bond. In some embodiments, this flowing of material may help to seal the perimeter about the external contact point. In some embodiments, the material sealing the perimeter of the external contact points may be liner material, adhesive, film, nonwoven, or combinations thereof.

In some embodiments, the method may further include directing at least a portion of the conductive material at least partially through a non-conductive material and sealing the non-conductive material about the external contact points. For example, an absorbent article may include a liquid impermeable backsheet and a liquid permeable liner positioned in facing relation. The absorbent article may further include a conductive material located between the backsheet and the liner wherein at least a portion of the conductive material extends at least partially through the backsheet to define external contact points. The backsheet may be sealed around the external contact points to retain liquid impermeability.

In some embodiments, the method may further include directing at least a portion of the conductive material at least partially through a non-conductive material without rupturing the conductive material to define one or more external contact points. In other words, portions of the conductive material may extend, at least partially, through a non-conductive material and remain intact at the location of the external contact points.

In some embodiments, the method may include directing at least a portion of the conductive material at least partially through a non-conductive material that is liquid impervious to define one or more external contact points without rupturing the conductive material. The method may further include sealing the non-conductive material around the external contact points thereby maintaining the liquid impermeability.

In some embodiments, the method may include providing a conductive material laminated with a masking material wherein the conductive material is oriented towards the outercover and the masking material is oriented towards the liner such that the conductive element is less visible from the liner side.

Any suitable bonding process may be used to extend and/or expose portions of the conductive material through non-conductive layers. In various embodiments, the bonding process may include ultrasonic bonding, thermal bonding, pressure bonding, and the like, and combinations thereof. In various embodiments, the bonding process may bond the liner to the backsheet in areas not including the conductive material. For example, the bonding process may include ultrasonic bonding using a plunge bonder available from Dukane Intelligent Assembly Solutions having offices at 2900 Dukane Drive, St. Charles, Ill., 60174, USA.

In various embodiments, the pressure on the bonder may be varied from 20 to 90 pounds per square inch (psi) and the power levels may be varied from 0 Joules to 100 Joules. In various embodiments, bond times may range from 0.1 to 1.0 seconds. Any suitable anvil pattern may be utilized. In some embodiments, the bonder may be a rotary bonder.

Figure 9:
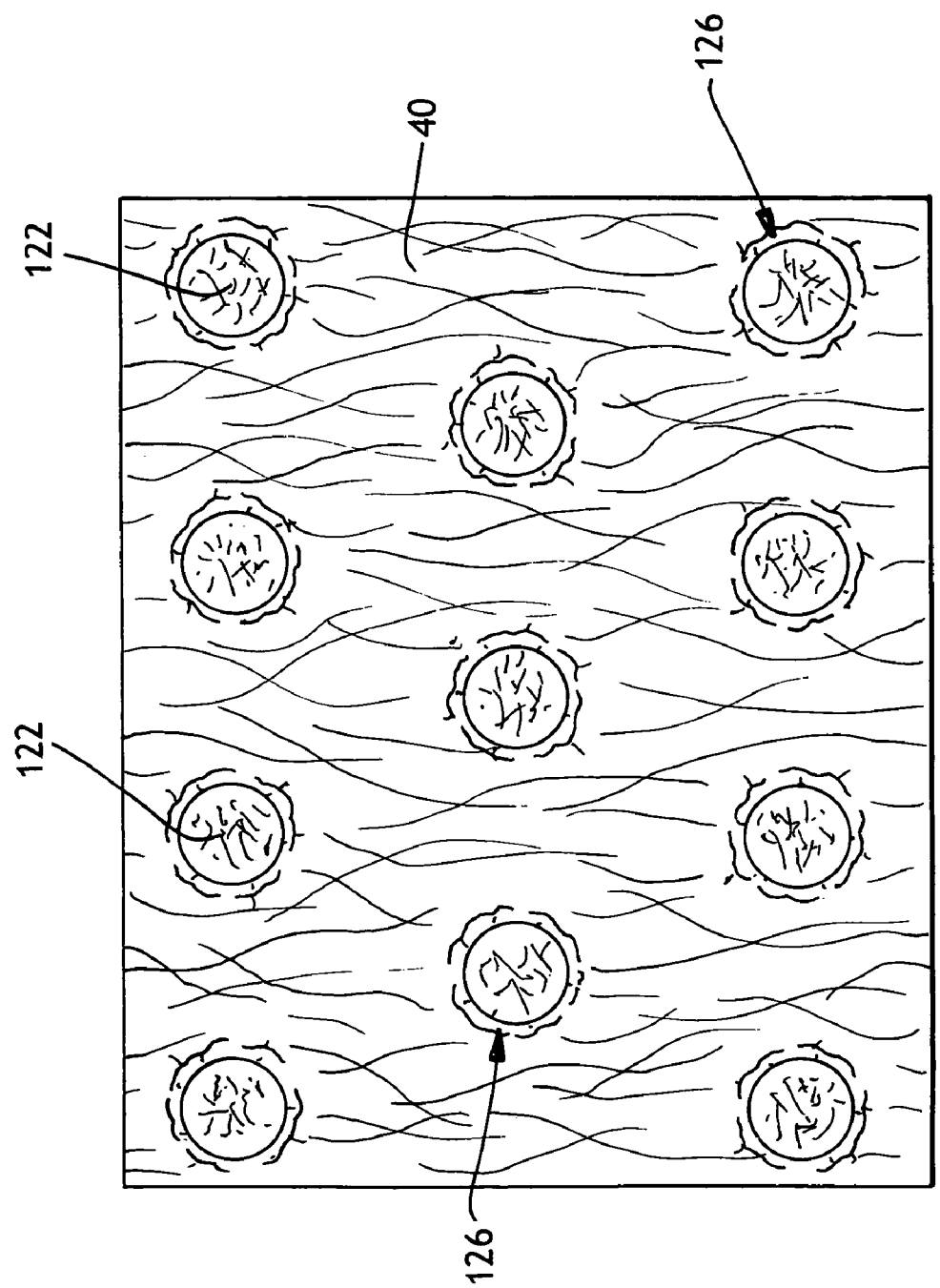
FIG. 9 is an optical image of a modified diaper illustrating exemplary external contact points.

In specific embodiments, suitable bonds were achieved at 50 psi, a power level of 50-60 Joules, and a bond time of 0.4 to 0.5 seconds. These bonds were created in diapers commercially available from Kimberly-Clark Corporation under the brand name HUGGIES® Disposable Diapers. The diapers were modified by inserting a conductor material between the backsheet and the absorbent structure. The conductor material was a foil laminate having 12 micron foil layer and a 12 micron thick polyester backing. The conductor material is available under the brand name NEPTCO 1001 laminated foil. FIG. 9 is an optical surface image of exemplary external contact points 122 exposed through the outercover 40. The optical surface image was obtained by using a WILD MAKROSCOP M420 stereo microscope equipped with sub-stage transmitted illumination and a ZEISS AXIOCAM color video camera. The stereo microscope's lens system was set to 8× magnification and incident lighting was provided by gooseneck fiber optics with a CUDA I-150 light source.

Referring to FIG. 9, a series of external contact points 122 are exposed through the outercover 40. The external contact points 122 are intact and are available for contact with a signaling device. The external contact points 122 define contact point perimeters 126 wherein the outercover 40 has been melted and sealed about the perimeter 126 thereby maintaining the liquid impermeability of the outercover 40 as a whole.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An absorbent article comprising, a liner and a outercover in facing relation; and at least one conductive element located between the liner and the outercover, wherein at least a portion of the conductive element is exposed through at least one of the liner and the outercover to define at least one external contact point and wherein the at least one external contact point defines a perimeter and wherein at least one of the liner and the outercover is sealed about the perimeter.

2. The absorbent article of claim 1 wherein at least one external contact point extends at least partially through the outercover.

3. The absorbent article of claim 1 wherein the conductive elements are intact proximate the external contact point.

4. The absorbent article of claim 1 wherein the conductive element is a laminate comprising a conductive layer and a masking layer.

5. The absorbent article of claim 4 wherein the conductive element is oriented towards the outercover and the masking layer is oriented towards the liner.

6. The absorbent article of claim 1 having a length and further comprising a first conductive element and a second conductive element, wherein both the first conductive element and the second conductive element extend the length of the absorbent article.

7. The absorbent article of claim 6 wherein the first conductive element and the second conductive element have a plurality of portions extending at least partially through the outercover to define a plurality of external contact points.

8. The absorbent article of claim 1 wherein the outercover and the liner are joined together at bond points that do not include the conductive element.

9. A kit comprising the absorbent article of claim 1 and a signaling device wherein the absorbent article includes a plurality of external contact points formed in the shape of a first indicia and the signaling device includes a second indicia wherein the first and second indicia aid alignment of the signaling device relative to the absorbent article.

10. An absorbent article having a length and comprising, a liner and an outercover in facing relation; and a first conductive element and a second conductive element located between the liner and the outercover and extending the length of the absorbent article, wherein a plurality of portions of the first conductive element and the second conductive element are at least partially exposed through the outercover to define a plurality of external contact points and wherein each external contact point defines a perimeter and the outercover is sealed about each perimeter.

11. The absorbent article of claim 10 wherein the liner and the outercover are joined together at bond points in areas not including the first or the second conductive elements.

12. The absorbent article of claim 10 wherein the plurality of external contact points are adapted to provide a first indicia for aligning a signaling device with the absorbent article to ensure electrical connectivity.

13. A kit comprising the absorbent article of claim 12 and a signaling device wherein the signaling device includes a second indicia adapted to align with the first indicia to ensure proper electrical connectivity.

14. A method of exposing portions of internally positioned conductive elements to an external surface of an absorbent article, comprising,
 providing an outercover and liner in facing relation with a conductive element located therebetween;
 at least partially exposing a portion of the conductive element through the outercover to define at least one external contact point on an outer article surface; and
 sealing the outercover about a perimeter of the at least one external contact point by at least partially melting portions of the outercover.

15. The method of claim 14 wherein the outercover, the liner, and the conductive element are provided as a part of an interconnected web of absorbent articles.

16. The method of claim 14 wherein the exposing step utilizes pressure bonding, ultrasonic bonding, or thermal bonding.

17. The method of claim 16 wherein the exposing step also extends the portion of the conductive element at least partially through the outercover.

18. The method of claim 14 wherein the steps of exposing a portion of the conductive element and sealing the outercover occur in the same operation.

19. The method of claim 14 wherein the conductive element is a laminate having a conductive layer and a masking layer and wherein the method further includes orienting the conductive layer towards the outercover and orienting the masking layer towards the liner.

20. The method of claim 14 further comprising bonding the outercover and the liner at bond points that do not include the conductive element in the same operation as the exposing step.

* * * * *